United States Patent [19]

Suhadolnik et al.

[11] Patent Number: 4,859,768
[45] Date of Patent: Aug. 22, 1989

[54] DERIVATIVES OF 2', 5'-OLIGOADENYLATE AND ANTIVIRAL USES THEREOF

[75] Inventors: Robert J. Suhadolnik, Roslyn, Pa.; Wolfgang Pfleiderer, Konstanz, Fed. Rep. of Germany

[73] Assignee: Temple University of the Commonwealth System of Higher Education, Philadelphia, Pa.

[21] Appl. No.: 144,602

[22] Filed: Jan. 11, 1988

Related U.S. Application Data

[63] Continuation of Ser. No. 629,660, Jul. 11, 1984, abandoned.

[51] Int. Cl.[4] .......................................... C07H 21/00
[52] U.S. Cl. ...................................... 536/27; 536/28; 536/29
[58] Field of Search ............................ 536/27, 28, 29

[56] References Cited

U.S. PATENT DOCUMENTS 4,464,359  8/1984  Suhadolnik et al. ............... 536/27
4,654,326  3/1987  Devash .............................. 536/27

OTHER PUBLICATIONS

Swai et al., The Journal of Biochemistry 258, No. 3, pp. 1671-1677, (1983).
Charubala et al., Tetrahedron Letters 21, pp. 4077-4080, (1980).
Eppstein et al., Virology 131, pp. 341-354, (1983).
Goswami et al., The Journal of Biochemistry 257, No. 12, pp. 6867-6870, (1982).
Devash et al., The Journal of Biological Chemistry 259, No. 6, pp. 3482-3486, (1984).

Primary Examiner—Johnnie R. Brown
Assistant Examiner—Jenny Tou
Attorney, Agent, or Firm—Seidel, Gonda, Lavorgna & Monaco

[57] ABSTRACT

Synthetic analogs of 2',5'-oligoadenylate wherein the aglycon, ribosyl moiety and/or terminal nucleoside have been modified are effective antiviral agents for pharmaceutical and agricultural use. They are particularly useful in inhibiting replication of tobacco mosaic virus. Novel synthetic analogs have the following formulae wherein $m=0, 1, 2$ and $3$ and $n=0, 1, 2, 3$ or $4$:

(Abstract continued on next page.)

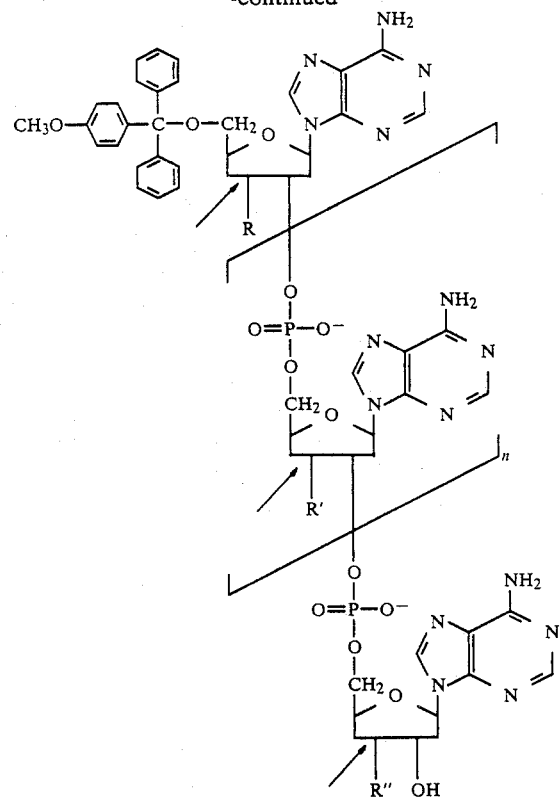
16 Claims, 1 Drawing Sheet

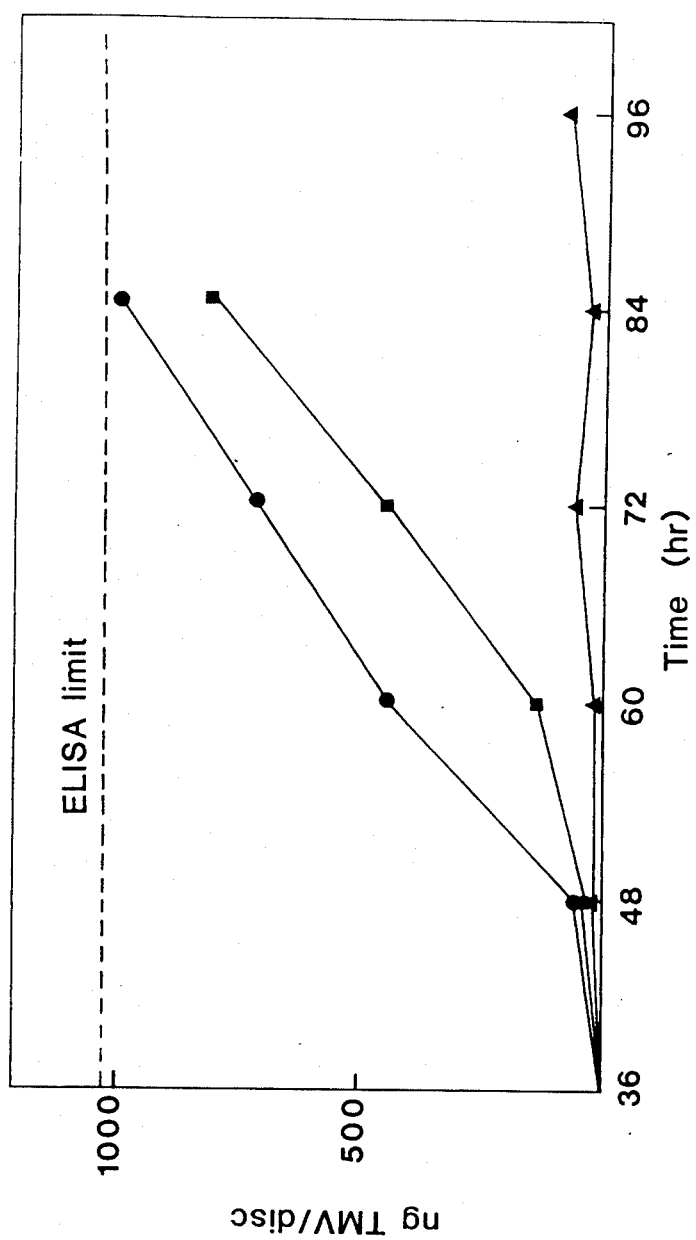

DERIVATIVES OF 2', 5'-OLIGOADENYLATE AND ANTIVIRAL USES THEREOF

REFERENCE TO GOVERNMENT GRANT

The invention described herein was supported by National Institutes of Health Grant GM-26134 and National Science Foundation Grant PCM-8111752.

This is a continuation of co-pending application Ser. No. 629,660, filed on July 11, 1984, abandoned.

FIELD OF THE INVENTION

The invention relates to a method of inhibiting viral infection in plants, particularly infection by tobacco mosaic virus, through the use of analogs of 2',5'-oligoadenylate wherein the aglycon ribosyl moiety and/or 2'-terminal nucleoside have been modified. This invention also relates to the preparation of novel analogs of 2',5'-oligoadenylate and 2',5'-oligo(3'-deoxyadenylate), and their antiviral uses in animals and plants.

BACKGROUND OF THE INVENTION

The full nomenclature of the subject matter of the present invention involves extremely long terms. It is customary for those skilled in the art to abbreviate these terms in a manner well known to them. These general and customary abbreviations are set forth herein below and will be utilized in the text of this specification.

Abbreviations

2',5'-oligo(A) or 2',5'-oligoadenylate or 2',5'-adenylate, oligomer of adenylic acid with 2',5'-phosphodiester linkages and a triphosphate at the 5'-end 2',5'-cordycepin analog or 2',5'-oligocordycepin, oligomer of 3'-deoxyadenylic acid with 2',5'-phosphodiester linkages and a triphosphate at the 5'-end 2',5'-$A_n$ or core oligomer, oligomer of adenylic acid with 2',5'-phosphodiester linkages 2',5'-$A_3$ or 2',5'-adenylate trimer core, adenylyl (2',5')adenylyl-(2',5')adenosine 2',5'-$A_4$ or 2',5'-adenylate tetramer core, adenylyl (2',5')adenylyl-(2',5')adenylyl(2',5')adenosine 2',5'-3'd$A_3$ or 2',5'-C-C-C or 2',5'-cordycepin trimer core, 3'-deoxyadenylyl(2',5')3'-deoxyadenylyl(2',5')3'-deoxyadenosine 2',5'-C-C-C-C or 2',5'-cordycepin tetramer core, 3'-deoxyadenylyl(2',5')3'-deoxyadenylyl(2',5')3'-deoxyadenylyl(2',5')3'-deoxyadenosine 2',5'-C-C-C 5'-monophosphate, 5'-O-phosphoryl-3'-deoxyadenylyl(2',5')3'-deoxyadenylyl(2',5')3'-deoxyadenosine 3',5'-$A_3$, adenylyl(3',5')adenylyl(3',5')adenosine 2',5'-$I_3$ or 2',5'-inosine trimer core, inosinylyl(2',5')inosinylyl(2',5')inosine 2',5'-oligoinosinate, oligomer of inosinate with 2',5'-phosphodiester linkages and a triphosphate at the 5'-end EBV, Epstein-Barr virus EBNA, Epstein-Barr virus associated early nuclear antigen HSV-1, Herpes simplex virus type 1

TMV, tobacco mosaic virus

NK, natural killer

A, adenosine (adenylate)

cordycepin or C or 3'-dA, 3'-deoxyadenosine(3'-deoxyadenylate)

ara-A, 9-$\beta$-D-arabinofuranosyladenine

3'-amino, 3'-amino-3'-deoxyadenosine tubercidin, 4-amino-7($\beta$-D-ribofuranosyl)pyrrolo[2,3-d]pyrimidine 3'-dATP, 3'-deoxyadenosine triphosphate ATP, adenosine triphosphate I, inosine (inosinate or inosinylyl)

Xylo A or xyloadenosine, 9-$\beta$-D-xylofuranosyladenine dCF or 2'-deoxycoformycin, (R)-3-(2-deoxy-$\beta$-D-erthropentofuranosyl)-3,6,7,8-tetrahydroimidazo[4,5-d][1,3]diazepine-8-ol 2',5'-A-A-Tu, adenylyl(2',5')adenylyl(2',5')tubercidin 2',5'-A-A-ara-A, adenylyl(2',5')adenylyl(2',5')ara-A 2',5'-C-C-A, 3'-deoxyadenylyl(2',5')3'-deoxyadenylyl(2',5')adenosine 2',5'-A-C-C, adenylyl(2',5')3'-deoxyadenylyl(2',5')3'-deoxyadenosine 2',5'-A-A-C, adenylyl(2',5')adenylyl(2',5')3'-deoxyadenosine 2',5'-xylo-$A_3$, xyloadenylyl(2',5')xyloadenylyl(2',5')xyloadenosine 2',5'-xylo-$A_4$, xyloadenylyl(2',5')xyloadenylyl(2',5')xyloadenylyl(2',5')xyloadenosine MMTr, 5'-O-p-methoxytrityl 2',5'-trityl-$C_3$, 5'-O-p-methoxytrityl-3'-deoxyadenylyl(2',5')3'-deoxyadenylyl(2',5')3'-deoxyadenosine 2',5'-trityl-$A_3$, 5'-O-p-methoxytrityladenylyl(2',5')adenylyl(2',5')adenosine 2',5'-C-C-dCF, 3'-deoxyadenylyl(2',5')3'-deoxyadenylyl(2',5')2'-deoxycoformycin 2',5'-A-A-3'-amino, adenylyl(2',5')adenylyl(2',5')3'-amino-3'-deoxyadenosine 2',5'-$A_{(Si)}$-$A_{(Si)}$-A, 3'-O-t-butyldimethylsilyladenylyl(2',5')3'-O-t-butyldimethylsilyladenylyl(2',5')adenosine 2',5'-C-A-C, 3'-deoxyadenylyl(2',5')adenylyl(2',5')3'-deoxyadenosine 2',5'-A-A-A-3'-O-pentyl, adenylyl(2',5-')adenylyl(2',5')3'-O-pentyladenosine 2',5'-A-A-A-3'-O-hexyl, adenylyl(2',5-')adenylyl(2',5')3'-O-hexyladenosine 2',5'-A-A-A-3'-O-heptyl, adenylyl(2',5-')adenylyl(2',5')3'-O-heptyladenosine 2',5'-A-A-C-C, adenylyl(2',5')adenylyl(2',5')3'-deoxyadenylyl(2',5')3'-deoxyadenosine Nature offers a wide variety of compounds that inhibit bacteria, inactivate viruses, and are cytotoxic to tumors. These naturally occurring metabolites have attracted much attention in terms of their use as biological probes in the study of cellular processes. The inventors have been concerned with the synthesis, biological characterization and use of nucleoside and nucleotide analogs in plant and animal systems.

With the expansion of the knowledge of the antiviral state induced by interferon, attention has been focused on the chemical and enzymatic synthesis and biological properties of the 2',5'-oligodenylates as mediators of the antiviral response. The inventors have chemically synthesized a number of 2',5'-oligoadenylate analogs with structural modifications that would provide biologically active molecules metabolically more stable than the naturally occurring 2',5'-oligoadenylate. The 2',5'-adenylate trimer and tetramer triphosphate analogs and their respective dephosphorylated "core" molecules have met these structural/biological goals in animal and plant systems. The concerted effort on the 2',5'-adenylate system developed from earlier studies by one of the inventors. In 1965, he was the first to report on the natural synthesis of the 2',5'-phosphodiester bond from cordycepin. (Cory, J. G., Suhadolnik, R. J., Resnick, B., and Rich, M. A., Biochim. Biophys. Acta 103, 646 (1965)). Subsequently, the inventors reported the enzymatic and chemical synthesis of 2',5'-cordycepin trimer and tetramer triphosphates and their respective cores. The enzymatic synthesis is disclosed in U.S. Pat. No. 4,464,359, which is specifically incorporated herein by reference.

SUMMARY OF THE INVENTION

Once the synthesis of 2',5'-oligocordycepin as a metabolically more stable 2',5'-oligoadenylate analog was demonstrated, the inventors determined that the 5'-dephosphorylated 2',5'-cordycepin trimer and tetramer cores inhibited virus replication, virus-induced morphological transformation, and tumor growth. Whereas 2',5'-cordycepin trimer core inhibits tumor growth in animals, the naturally occurring 2',5'-adenylate trimer core is not inhibitory.

The inventors have synthesized additional trimer cores containing adenylate and cordycepin residues. These molecules have the general formula, 2',5'-A-A-C and 2',5'-A—C—C where A=adenylate and C=cordycepin. These molecules have been found to inhibit ascites tumor growth and morphological transformation of EBV-infected lymphocytes.

The inventors have also synthesized 2',5'-adenylate trimer core analogs with modifications at the 2'-terminal adenylate. These compounds have the general formula, 2',5'-A-A-R, where R=tubercidin, ara-A or 3'-amino-3'-deoxyadenosine. These molecules have been found to inhibit ascites tumor growth and morphological transformation of EBV-infected lymphocytes. Preparation of the trimer core 2',5'-A-A-ara-A is carried out by condensing the nucleoside $N^6,2'$-O-,3'-O-tribenzoylarabinofuranosyladenine with the fully protected $N^6$,3'-O-dibenzoyl-5'-O-trityladenylyl(2'-O-tribromoethyl-5')$N^6$,3'-O-dibenzoyladenosine-2'-(tribromoethylcyanoethylphosphate) using as the coupling reagent quinoline-8-sulfonyl-3-nitro-1,2,4-triazolide. The final deprotection of the resulting trimer triester is performed by detritylation with boron trifluoride/methanol followed by electrochemical deblocking (CH$_3$CN, Hg pool, NaHCO$_3$ in the anolyte) of the tribromoethyl moiety. The debenzoylation of the diester is accomplished using butylamine/methanol to form adenylyl(2',5')adenylyl(2',5')9-b-D-arabinofuranosyladenine. This procedure is reported in Engels, J., Tetrahedron Lett. 21, 4339 (1980) which is specifically incorporated herein by reference.

The 5'-terminus of the 2',5'-adenylate trimer core molecule has been modified by the addition of a 5'-O-p-methoxytrityl group (MMTr). These molecules have the general formula 2',5'-trityl-A$_3$ and 2',5'-trityl-C$_3$. They inhibit EBV-induced morphological transformation.

It has been reported that the naturally occurring 2',5'-oligoadenylate 5'-triphosphate protects plant tissue from infection by tobacco mosaic virus (TMV) (Devash, Y., Biggs, S., and Sela, I., Science 216, 1415 (1982)). The authors reported that replication of TMV was reduced 80–90%.

The inventors have prepared the 5'-dephosphorylated 2',5'-cordycepin trimer core and compared it with the 2',5'-oligoadenylate 5'-triphosphate and its trimer core in inhibiting TMV replication. It was observed that at $2 \times 10^{-7}$M, 2',5'-adenylate trimer core only inhibits TMV replication for 48 hours with tobacco leaf discs, whereas the 2',5'-cordycepin trimer core completely inhibits TMV replication for 96 hours. Similarly, the 2',5'-cordycepin trimer core inhibited TMV replication 99% in *N. glutinosa* leaves, whereas the 2',5'-adenylate trimer core inhibited only 93%. The 99% inhibition of TMV replication by 2',5'-cordycepin trimer core was determined to be due to $1 \times 10^{-12}$ moles of 2',5'-cordycepin trimer core per cm$^2$ of plant leaf.

The 2',5'-adenylate trimer core and 2',5'-cordycepin trimer core were further structurally modified by the inventors to 2',5'-I$_3$, to 2',5'A-A-ara-A and to 2',5'-A-A-Tu. These analogs inhibited TMV replication in plant leaves by 92, 94, and 95%, respectively.

According to the present invention, the 2',5'-cordycepin trimer core and other structurally modified 2',5'-adenylate core molecules inhibit virus-induced transformation of human cells, HSV-1 replication, and growth of ascites and solid tumors. Surprisingly, these molecules inhibit virus replication in plants.

The novel compounds of the present invention useful in inhibiting virus infections in plants and mammals have the general formula:

wherein
m = 0, 1, 2 or 3
n = 0, 1, 2, 3 or 4
R and R' are selected from the group consisting of hydrogen, hydroxyl and —OSi(CH$_3$)$_2$—C(CH$_3$)$_3$, but where n is greater than 1, each R' need not be identical
X is selected from the group consisting of

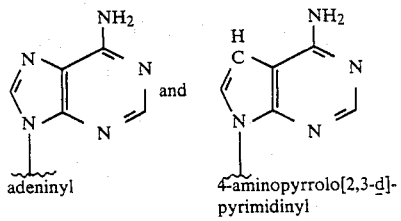

adeninyl  4-aminopyrrolo[2,3-d]-pyrimidinyl

R″ and R‴ are selected from the group consisting of hydroxyl, hydrogen, —NH$_2$, —OC$_{n'}$H$_{n''}$ where n′ and n″ are intergers greater than one, and —OSi(CH$_3$)$_2$—C(CH$_3$)$_3$ except that where X is adeninyl, then R″ may not be hydroxyl if R, R′ and R‴ are hydroxyl,
R″ may not be hydrogen if R and R′ are hydrogen and R‴ is hydroxyl,
R″ may not be hydrogen if R and R′ are hydroxyl.

The preferred compounds comprise the 5′ mono-, di-, and triphosphates of the following 2′,5′ trimer and tetramer cores:

2′,5′-C-C-A, or 3′-deoxyadenylyl(2′,5′)3′-deoxyadenylyl(2′,5′)adenosine

2′,5′-A-C-C, or adenylyl(2′,5′)3′-deoxyadenylyl(2′,5′)3′-deoxyadenosine

2′,5′-C-A-C, or 3′-deoxyadenylyl(2′,5′)adenylyl(2′,5′)3′-deoxyadenosine

2′,5′-C-C-dCF, or 3′-deoxyadenylyl(2′,5′)3′-deoxyadenylyl(2′,5′)(R)-3-(2-deoxy-β-D-erythropentofuranosyl)3,6,7,8-tetrahydroimidazo[4,5-d][1,3]diazepine-8-ol 2′,5′-A-A-3′-amino, or adenylyl(2′,5′)adenylyl(2′,5′)3′-amino-3′-deoxyadenosine 2′,5′-A$_{(Si)}$-A$_{(Si)}$-A, or 3′-O-t-butyldmethylsilyladenylyl(2′,5′)3′-O-t-butyldimethylsilyladenylyl(2′,5′)adenosine 2′,5′-A-A-A-3′-O-pentyl, or adenylyl(2′,5′)adenylyl(2′,5′)3′-O-pentyladenosine 2′,5′-A-A-A-3′-O-heptyl, or adenylyl(2′,5′)adenylyl(2′,5′)3′-O-heptyladenosine 2′,5′-A-A-C-C, or adenylyl(2′,5′)adenylyl(2′,5′)3′-deoxyadenylyl(2′,5′)3′-deoxyadenosine.

Most preferred are 2′,5′-A$_{Si}$-A$_{Si}$-A, or 3′-O-t-butyldimethylsilyladenylyl(2′,5′)3′-O-t-butyldimethylsilyladenylyl(2′,5′)adenosine; 3′-deoxyadenylyl(2′,5′)3′-deoxyadenylyl(2′,5′)3′-deoxyadenosine; xyloadenylyl(2′,5′)xyloadenylyl-(2′,5′)xyloadenosine; adenylyl(2′,5′)adenylyl(2′,5′)tubercidin; xyloadenylyl(2′,5′)xyloadenylyl(2′,5′)xyloadenylyl(2′,5′)xyloadensoine; adenylyl(2′,5′)adenylyl(2′,5′)3′-deoxyadenosine; and 3′-deoxyadenylyl(2′,5′)3′-deoxyadenylyl(2′,5′)3′-deoxyadenylyl(2′,5′)3′-deoxyadenosine.

Other novel compounds of the present invention useful in inhibiting virus infections in plants and mammals have the following general formula:

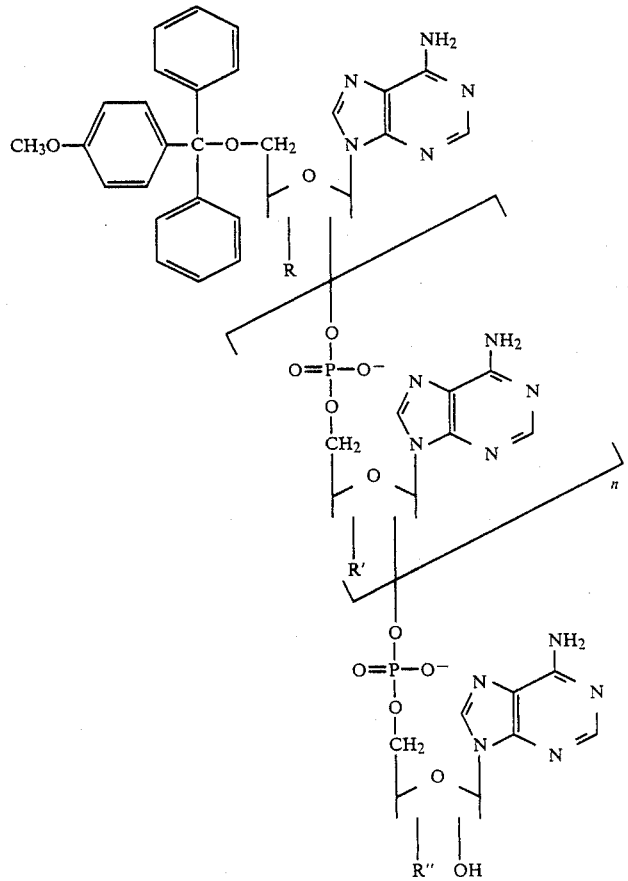

wherein
n=0, 1, 2, 3 or 4, and
R, R′ and R″ are selected from the group consisting of hydrogen, hydroxyl, —NH$_2$, —OC$_{n'}$H$_{n''}$ where n′ and n″ are integers greater than one, and —OSi(CH$_3$ )$_2$—C(CH$_3$)$_3$. Preferred compounds are the mono-, di-, and triphosphates of the following trimer cores:

2',5'-trityl-C$_3$, or 5'-O-p-methoxytrityl-3'-deoxyadenylyl(2',5')3'-deoxyadenylyl(2',5')3'-deoxyadenosine 2',5'-trityl-A$_3$, or 5'-O-p-methoxytrityladenylyl(2',5')adenylyl(2'5')adenosine Most preferred is 5'-O-p-methoxytrityladenylyl(2',5')adenylyl(2',5')adenosine.

A method of inhibiting viral infection in plants is provided comprising administering one or more compounds which comprise synthetic derivatives of 2',5'-oligoadenylate. One class of preferred compounds has the general formula:

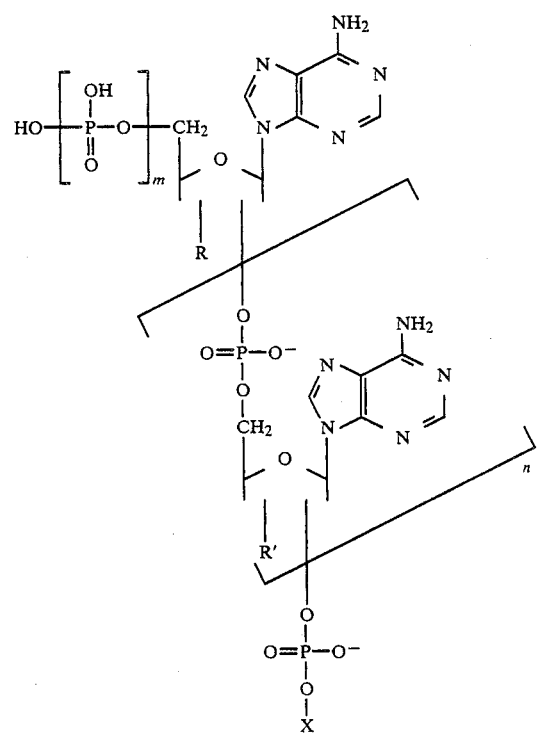

wherein m=0, 1, 2 or 3 n=0, 1, 2, 3 or 4

R and R' are selected from the group consisting of hydrogen and hydroxyl, and

X is selected from the group consisting of:

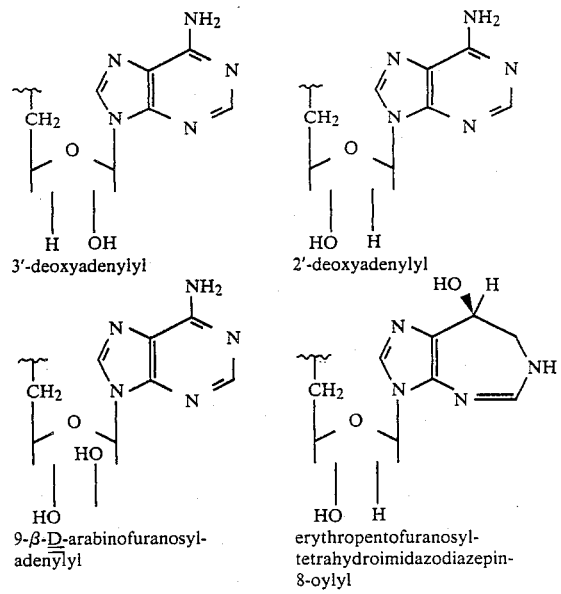

3'-deoxyadenylyl

2'-deoxyadenylyl

9-β-D-arabinofuranosyladenylyl erythropentofuranosyltetrahydroimidazodiazepin-8-oylyl Most preferred is adenylyl(2',5')adenylyl(2',5')9-b-D-arabinofuranosyladenine.

Another class of preferred compounds used to inhibit viral infection in plants has the following general formula wherein m=0, 1, 2 or 3 and n=0, 1, 2, 3 or 4:

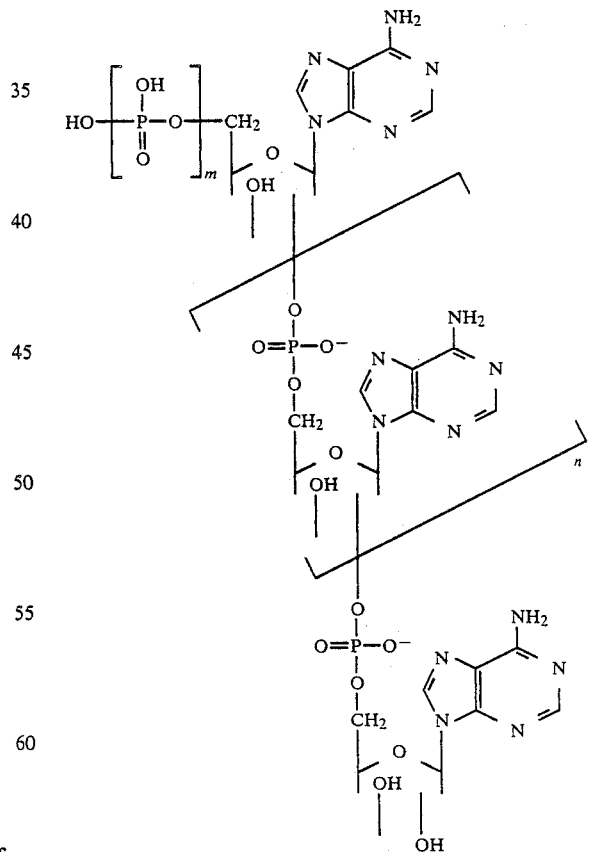

The 2',5'-oligoadenylate analogs have utility in inhibiting the growth of virus in plants and animals. They are active in inhibiting the transformation of Epstein Barr virus in human lymphocytes in the absence of interferon. They inhibit ascites tumor growth. They are active in inhibiting replication of Herpes simplex virus type 1 in human fibroblast monolayers in the absence of interferon. Thus, administration of the compounds of the present invention comprises a method of controlling viral infection in mammals.

For pharmaceutical use, the compounds of the present invention may be taken up in pharmaceutically acceptable carriers, for example, solutions, suspensions, tablets, capsules, ointments, elixirs, and injectable compositions and the like and administered to subjects suffering from viral infection, the dosage administered depending upon the severity of the infection and the size and weight of the infected subject.

The 2',5'-oligoadenylate analogs also possess antiviral activity against plant-infecting viruses, particularly tobacco mosaic virus. Inhibition of replication was determined in tobacco leaf discs, protoplasts and whole tobacco plants, using infectivity tests and enzyme-linked immunosorbent assays.

The 2',5'-oligoadenylate analogs may be administered effectively to plants by topical application by abrasion of the lead surface, aerosol spray, treatment of the soil, spraying or dusting. An effective antiviral composition may be formed by combining one or more of the 2',5'-oligoadenylate analogs with a suitable carrier material. The active compound may also be administered by spraying insect vectors such as aphids, thrips and whiteflies which carry virus to plants. The dosage administered depends upon the severity of the infection.

The 2',5'-oligoadenylate analogs may be applied to plant seeds prior to germination to control viruses contained in the germ plasm. The seeds may be soaked in a solution of polyethylene glycol ("PEG") containing one or more 2',5'-oligoadenylate analogs. PEG brings the seeds to physiological activity and arrest. The relative concentration of active compound to PEG depends upon the type of seed under treatment.

The 2',5'-oligoadenylate analogs also have utility in protecting plant cells in liquid culture from viral infection.

BRIEF DESCRIPTION OF THE FIGURE

The FIGURE shows the time course of TMV replication in the presence of 2',5'-adenylate trimer core or 2',5'-cordycepin trimer core, up to 96 hours.

DETAILED DESCRIPTION OF THE PREFERRED EMBODIMENTS

The novel 2',5'-oligoadenylate analogs of the present invention may be chemically synthesized as follows. A blocked adenosine-2'-phosphodiester is prepared by blocking the 6-amino position with benzoyl, blocking the 5' position with p-methoxytrityl and optionally blocking the 3' position with t-butyldimethylsilyl. A blocked nucleoside is prepared by blocking the 2' and 3' positions with acetyl, benzoyl or t-butyldimethylsilyl. Preparation of suitably blocked adenosine-2'-phosphodiesters is carried out by adding the t-butyldimethylsilyl group to the 3'-O-t-butyldimethylsilyl-isomeric-3'-hydroxyl group of N6-benzoyl-5'-O-(4-methoxytrityl)adenosine by condensing the latter compound with t-butyldimethylsilylchloride using imadazole in pyridine to yield the 3'-O-t-butyldimethylsilyl derivative. Phosphorylation of the derivative is carried out using 2,5-dichlorophenyl-phosphorotriazolide in pyridine to yield a suitably blocked adenosine-2'-phosphodiester. This preparation is described in R. Charubala, E. Uhlmann, and W. Pfleiderer, Liebigs Ann. Chem., 2392 (1981) and R. Charubala, W. Pfleiderer, Tetrahedron Letters 21, 4077 (1980), which are specifically incorporated herein by reference. The blocked adenosine-2'-phosphodiester is condensed with the blocked nucleoside in the presence of a condensing reagent which causes blocking of the phosphate functions to form a fully protected dinucleosidemonophosphotriester.

The resulting fully protected condensate is then detritylated at the terminal 5' position with a detritylating agent and condensed with a further adenosine-2'-phosphodiester, blocked as described above, to form a fully protected 2',5'-trinucleosidediphosphoditriester, or 2',5' trimer core. The fully protected trimer core is then treated with appropriate deprotecting reagents to achieve complete deprotection and conversion to 2',5' trimer core.

Preparation of the novel 2,',5'oligoadenylate analogs is illustrated in the following non-limiting examples. The most preferred analogs of this invention can all be prepared by the method of the following examples as well as by the methods set out in U.S. Pat. No. 4,464,359 which is specifically incorporated herein by reference for that disclosure.

EXAMPLE 1

Preparation of Structurally Modified 2',5'-Adenylate Trimer Cores

The various structurally modified novel trimer core analogs of 2',5'-adenylate may generally be prepared as follows.

One mmole of suitably blocked adenosine-2'-phosphodiester having the general formula of reactant (I) was prepared from adenosine or cordycepin according to the method of Charubala, R., Uhlmann, E., and Pfleiderer, W., Liebigs Ann. Chem., 2392 (1981) and Charubala, R., and Pfleiderer, W., Tetrahedron Lett. 21, 4077 (1980). Examples of suitably blocked adenosine-2'-phosphodiesters are represented by compounds 1 and 2, listed in Table 1.

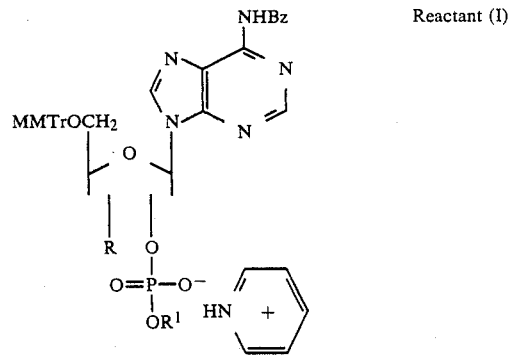

TABLE 1

| Compound Name | Compound No. | R | R¹ |
|---|---|---|---|
| Pyridinium N⁶—benzoyl-3'-O—t-butyldimethylsilyl-5'-O—p-methoxytrityladenosine-2'-(2-chlorophenyl)-phosphate | 1 | OSi—⧺ | —⟨⟩—Cl |

TABLE 1-continued

| Compound Name | Compound No. | R | R¹ |
|---|---|---|---|
| Pyridinium $N^6$—benzoyl-5'-O—p-methoxytrityl-3'-deoxyadenosine-2'-(2-chlorophenyl)-phosphate | 2 | H | 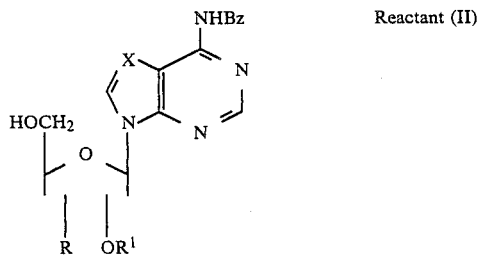 |

Reactant (I) was combined with a blocked nucleoside having the general formula of reactant (II) below. Reactant (II) is exemplified by compounds 3–9 listed in Table 2.

Compounds 3 and 9 are prepared treating $N^6$-benzoylated adenosine with monomethoxytrityl chloride in pyridine to yield the 5'-monomethoxytrityl derivative. The derivative is treated with t-butyldimethylsilylchloride in a mixture of pyridine and methylimidazole to form the $N^6$-benzoyl-2',3'-di-O-t-butyldimethylsilyl-5'-monomethoxytrityl adenosine. The trityl group is removed by acetic acid to produce compound 3. Compound 9 is synthesized analogously, starting with $N^6$-benzoylated tubercidin. This method of preparation is as described in Charubala et al, Liebigs Ann. Chem. 2392 (1981). Compound 4 is prepared by treating $N^6$-benzoylated-3'-deoxyadenosine with monomethoxytritylchloride to yield $N^6$-benzoyl-5'-O-monomethoxytrityl-3'-deoxyadenosine (cordycepin) which is converted to $N^6$-2'-O-dibenzoyl-3'-deoxyadenosine by benzoylation of the 2'-hydroxyl group with benzoylchloride followed by detritylation with 80% acetic acid for 30 minutes. This method of preparation is as described in Tetrahedron Lett. 21, 4077 (1980). Compound 5 is prepared by converting $N^6$-benzoyladenosine with t-butyldiphenylchlorosilane to the 5'-silylated nucleoside in pyridine. The 5'-silylated nucleoside is treated with triethyl orthoacetate followed by boron trifluoride/diethyl ether and sodium iodide in $CH_3CN$ (0° C., 1

TABLE 2

| Compound Name | Compound No. | R | R¹ | X |
|---|---|---|---|---|
| $N^6$—benzoyl-2',3'-di-O—t-butyldimethylsilyl-adenosine | 3 | OSi—⊞— | Si—⊞— | N |
| $N^6$,2'-O—dibenzoyl-3'-deoxyadenosine | 4 | H | Bz | N |
| $N^6$—benzoyl-2'-O—acetyl-3'-deoxyadenosine | 5 | H | Ac | N |
| $N^6$,2'-O—dibenzoyl-3'-O—n-pentyladenosine | 6 | O—n-$C_5H_{11}$ | Bz | N |
| $N^6$,2'-O—dibenzoyl-3'-O—n-heptyladenosine | 7 | O—n-$C_7H_{15}$ | Bz | N |
| $N^6$—benzoyl-2'-O—t-butyldimethylsilyl-3'-p-nitrophenyl-ethoxycarbonylamino-3'-deoxyadenosine | 8 | NHCOOCH₂CH₂—⟨⟩—NO₂ | Si—⊞— | N |
| 2',3'-di-O—t-butyl-dimethylsilyl-tubercidin | 9 | OSi—⊞— | Si—⊞— | CH |

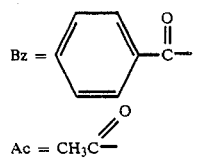

Ac = $CH_3\overset{O}{\underset{\|}{C}}$—

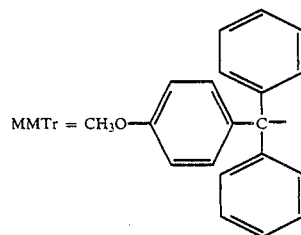

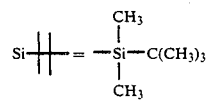

hour) to yield the 3'-iodoacetyl derivative. The iodoacetyl derivative is converted to compound 5 by treatment with tributyltinhydride in toluene (80° C., 1 hour) and desilylation with ammonium tetrabutyl fluoride in tetrahydrofuran. This method of preparation is as described by Engles, J., in Tetrahedron Lett. 21, 4339 (1980), which is incorporated herein by reference. Compounds 6 and 7 are prepared by treating $N^6$-benzoyl adenosine with tritylchloride in pyridine and refluxing for 2 hours. $N^6$-benzoyl-5'-trityladenosine is isolated by extraction with chloroform. The water from the chloroform phase is removed by drying with sodium sulfate. $N^6$-benzoyl-2',5'-di-O-trityladenosine and $N^6$-benzoyl-3',5'-di-O-trityladenosine are isolated by preparative silica gel thin layer chromatography in chloroform/ethanol. Compounds 6 and 7 are prepared by treating the isolated compounds with n-pentylchloride and n-heptylchloride, respectively, under reflux in a suspension of sodium hydroxide in benzene. The solution is neutralized by refluxing in acetic acid followed by the addition of diethyl ether and water. The reaction products are extracted with chloroform followed by thin layer chromatography with chloroform:methanol (4:1) on silica gel plates. The trityl and benzoyl groups are removed by refluxing in acetic acid for one hour, cooling, extraction with diethyl ether, followed by concentration and cooling to yield crystalline compounds 6 and 7. This method of preparation is carried out according to Blank, H. U., Frahne, D., Myles, A. and Pfleiderer, W., Justus Liebigs Ann. Chem. 742, 34 (1970), which is incorporated herein by reference. Compound 8 was prepared as follows. 1 mmole of 3'-amino-3'-deoxyadenosine was reacted with 1.2 mmole of 1-methyl-3-nitrophenylethoxy carboxylimidazolium chloride in dimethylformamide, followed by the addition of hexamethyldisilazane to block the 2', 5' and 6-amino positions. 1.1 mmole of benzoyl chloride in pyridine was added at room temperature to produce blocked $N^6$-benzoyl-2',5'-disilyladenosine. The reaction mixture was poured into methanol-$NH_3$ to remove the 2' and 5' silyl groups. Reaction with MMTr chloride in pyridine yielded the 5'-MMTr derivative. Tert-butyldimethylsilyl chloride in a mixture of pyridine and 1-methylimidazole was then added to the 5'-MMTr derivative and 5'-detritylated as in Example 1 to form compound 8.

Reactants (I) and (II) were combined to produce the intermediate having the general formula of dimer (III) as follows. 0.95 Mmole of reactant (II) and condensing reagents 2,4,6-triisopropylbenzenesulfonyl chloride (2 mmole) and 1-methylimidazole (6 mmole) were combined and stirred for 1 hr at room temperature. The reaction is stopped by adding 30 ml of aqueous phosphate buffer pH 7 and extracted with 150 ml of chloroform. The chloroform layer was washed twice with 50 ml of water, dried over sodium sulfate about 1-2 hr and filtered. The chloroform was evaporated to a small volume and then applied to a silica gel column (20×2.5 cm) for purification. Chromatography was performed first with chloroform and then with chloroform/methanol (99/1, v/v) to elute the fully protected dinucleosidemonophosphotriester product of the general formula of dimer (III). Evaporation gave a solid foam of dimer (III) exemplified by compounds 10–17 (Table 3).

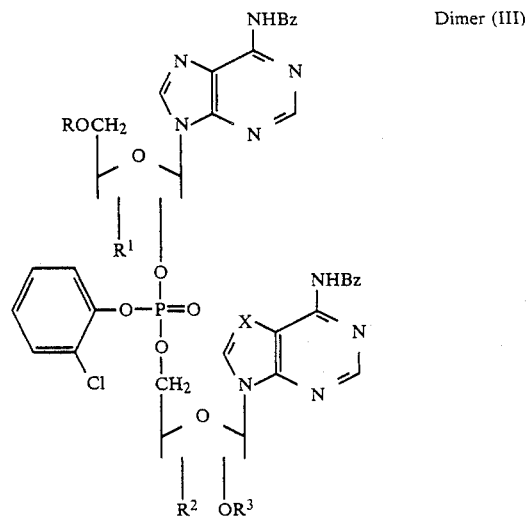

Dimer (III)

TABLE 3

| Compound No. | R | $R^1$ | $R^2$ | $R^3$ | X | Compound No. | R |
|---|---|---|---|---|---|---|---|
| 10 | MMTr | OSi-\|\|- | OBz | Bz | N | 18 | H |
| 11 | MMTr | OSi-\|\|- | H | Ac | N | 19 | H |
| 12 | MMTr | OSi-\|\|- | OSi-\|\|- | Si-\|\|- | CH | 20 | H |
| 13 | MMTr | OSi-\|\|- | O—n-$C_5H_{11}$ | Bz | N | 21 | H |
| 14 | MMTr | OSi-\|\|- | O—n-$C_7H_{15}$ | Bz | N | 22 | H |
| 15 | MMTr | H | OBz | Bz | N | 23 | H |
| 16 | MMTr | H | H | Bz | N | 24 | H |

TABLE 3-continued

| Compound No. | R | R¹ | R² | R³ | X | Compound No. | R |
|---|---|---|---|---|---|---|---|
| 17 | MMTr | OSi—∥— | NHCOOCH₂CH₂—⟨C₆H₄⟩—NO₂ | Si—∥— | N | 25 | H |

One mmole of the fully protected dimer (III) was stirred at room temperature for 30 minutes in 20 ml of 2% p-toluenesulfonic acid in dichloromethane/methanol (4/1, v/v) for detritylation. 20 ml of phosphate buffer pH 7 was added and subsequently extracted several times with 200 ml of dichloromethane. The organic phase was washed with water, dried over sodium sulfate, evaporated to a small volume and then applied to a silica gel column (20×2.5 cm) for purification. Elution was performed with chloroform (400 ml) followed by chloroform/methanol (98/2, v/v). Evaporation of the main fraction gave a 80–90% yield of the detritylated dinucleosidemonophosphotriester (dimer (III)), exemplified by compounds 18–25, (Table 3).

The fully protected 2′,5′-trinucleosidediphosphoditriester, having the general formula of trimer (IV) and exemplified by compounds 26–34 (Table 4, below), was prepared from the 5′-detritylated dimer (III) as follows.

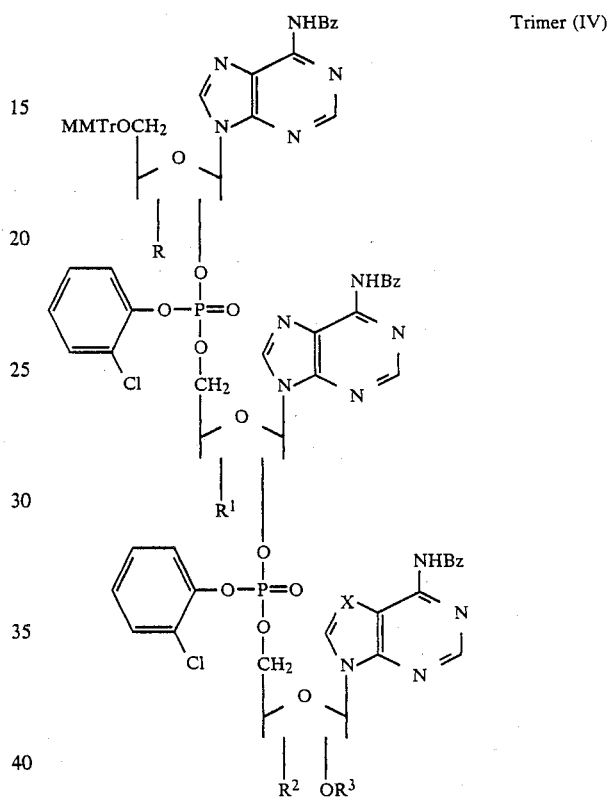

Trimer (IV)

TABLE 4

| Compound No. | R | R¹ | R² | R³ | X |
|---|---|---|---|---|---|
| 26 | H | OSi—∥— | OBz | Bz | N |
| 27 | H | OSi—∥— | H | Ac | N |
| 28 | OSi—∥— | OSi—∥— | OSi—∥— | Si—∥— | CH |
| 29 | OSi—∥— | OSi—∥— | O—n-C₅H₁₁ | Bz | N |
| 30 | OSi—∥— | OSi—∥— | O—n-C₇H₁₅ | Bz | N |
| 31 | OSi—∥— | OSi—∥— | OBz | Bz | N |
| 32 | H | H | OBz | Bz | N |

TABLE 4-continued

| Compound No. | R | R¹ | R² | R³ | X |
|---|---|---|---|---|---|
| 33 | OSi–╫ | H | H | Bz | N |
| 34 | OSi–╫ | OSi–╫ | NHCOOCH₂CH₂–⟨C₆H₄⟩–NO₂ | Si–╫ | N |

1.05 Mmole of the starting adenosine-2'-phosphodiester (reactant (I)), was condensed with 1 mmole of the 5'-detritylated dimer (III) (compounds 18–25) in 10 ml of absolute pyridine using 3 mmole of 2,4,6-triisopropylbenzenesulfonyl chloride and 9 mmole of 1-methylimidazole as condensing agents. Work-up was performed after 2 hr in the manner as described above. Quenching with phosphate buffer, followed by extraction with dichloromethane and silica gel chromatography in chloroform and chloroform/methanol (99/1 to 98/2, v/v) yielded 70–90% of fully protected trimer (IV) (compounds 26–34), as a chromatographically pure amorphous powder.

The fully protected 2',5'-trinucleosidediphosphoditriester, trimer (IV), was deprotected to trimer core (V) as follows.

0.01 Mole of trimer (IV) was treated with a solution of 0.073 g p-nitrobenzaldeoxime and 0.07 g tetramethylguanidine in 2 ml of dioxane water (1/1, v/v) for 16 hrs at room temperature to deblock the o-chlorophenyl group. After evaporation to dryness and coevaporation four times with water, 20 ml of concentrated ammonium hydroxide was added and the solution stirred for 2 days at room temperature to deprotect the acyl groups. The solution was then evaporated again, and the residue was dissolved in 25 ml of water and washed for times with 10 ml of chloroform each time. The water layer was evaporated to dryness and coevaporaed ten times with 10 ml absolute pyridine each time. The residue was then treated with 2 ml of an 0.5M solution of anhydrous tetrabutylammonium fluoride in absolute pyridine for 16 hrs to remove the t-butyldimethylsilyl groups. After evaporation, treatment of the residue with 5 ml of 80% acetic acid for 6 hrs at room temperature lead to cleavage of the p-methoxytrityl group. The solution was again evaporated, the residue dissolved in 15 ml of water, and extracted four times with 5 ml of chloroform each time. The aqueous layer was evaporated and then coevaporated several times with water until the smell of acetic acid disappeared. The residue was dissolved in 10 ml of water and applied to a DEAE-Sephadex A-25 column (60×1 cm) for ion-exchange chromatography with a gradient of 0.001–0.5M triethylammonium bicarbonate. The main fraction was evaporated, then coevaporated several times with water. Trimer core (V), a fully deprotected 2',5'-trinucleosidediphosphate, was isolated by lyophilization of the aqueous solution to give 70–90% of an amorphous solid. Trimer core (V) is exemplified by compounds 35–45 (Table 5).

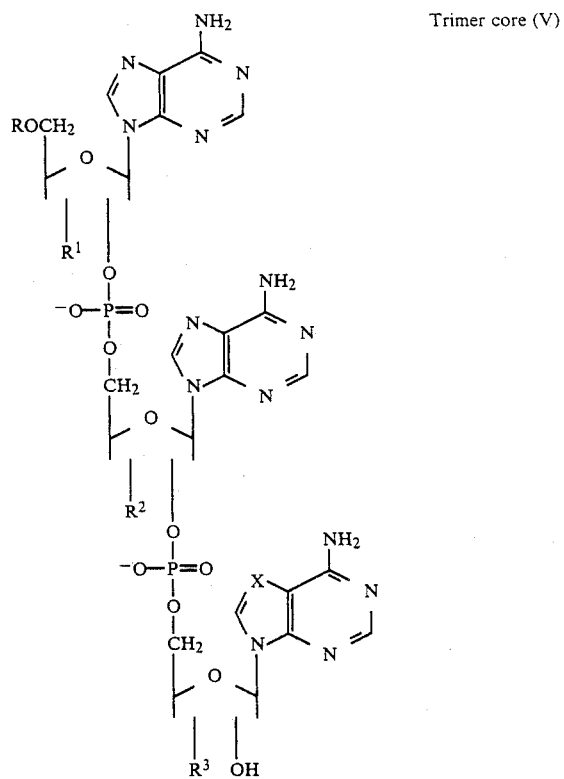

Trimer core (V)

TABLE 5

| Compound Name | Compound No. | R | R¹ | R² | R³ | X |
|---|---|---|---|---|---|---|
| 2',5'-A—A—C | 35 | H | OH | OH | H | N |
| 2',5'-C—A—C | 36 | H | H | OH | H | N |
| 2',5'-A—A—Tu | 37 | H | OH | OH | OH | CH |
| 2',5'-A—A—A—3'-O—pentyl | 38 | H | OH | OH | O—n-C₅H₁₁ | N |
| 2',5'-A—A—A—3'-O—heptyl | 39 | H | OH | OH | O—n-C₇H₁₅ | N |
| 2',5'-A(Si)—A(Si)—A | 40 | H | OSi++ | OSi++ | OH | N |
| 2',5'-C—C—A | 41 | H | H | H | OH | N |
| 2',5'-A—C—C | 42 | H | OH | H | H | N |
| 2',5'-A—A—3'-amino | 43 | H | OH | OH | NH₂ | N |
| 2',5'-Trityl—A₃ | 44 | MMTr | OH | OH | OH | N |

TABLE 5-continued

| Compound Name | Compound No. | R | R¹ | R² | R³ | X |
|---|---|---|---|---|---|---|
| 2',5'-Trityl—C₃ | 45 | MMTr | H | H | H | N |
| 2',5'-C—C—C—5'-monophosphate | 46 | H₂O₃P | H | H | H | N |

EXAMPLE 2

Preparation of 3'-O-t-butyldimethylsilyladenylyl (2',5')3'O-t-butyldimethylsilyladenylyl(2',5')adenosine 0.01 Mmole of N⁶-benzoyl-3'-O-t-butyldimethylsilyl--5'-O-p-methoxytrityladenylyl(2'-o-chlorophenyl-5')N⁶-benzoyl-3'-O-t-butyldimethylsilyladenylyl(2'-o-chlorophenyl-5')N⁶,2'-O,3'-O-tribenzoyladenosine (compound 31, Table 4) was treated according to the procedure of Example 1, except that the deprotection step of treatment with tetrabutylammoniumfluoride was omitted, in order to produce 2',5'-A$_{(Si)}$-A$_{(Si)}$-A (compound 40, Table 5).

EXAMPLE 3

Preparation of adenylyl(2',5')adenylyl (2',5')3'-amino-3'-deoxyadenosine 0.01 Mmole of N⁶-benzoyl-3'-O-t-butyldimethylsilyl-5'-O-p-methoxytrityladenylyl(2'-o-chlorophenyl-5')N⁶-benzoyl-3'-O-t-butyldimethylsilyladenylyl(2'-o-chlorophenyl-5')N⁶-benzoyl-2'-O-t-butyldimethylsilyl-3'-p-nitrophenylethoxycarbonylamino-3'-deoxyadenosine (compound 34, Table 4) was treated according to the deprotection procedure of Example 1 wherein the p-nitrophenylethoxycarbonyl group was cleaved simultaneously with the silyl groups by tetrabutylammonium fluoride in a β-elimination process. Subsequent decarboxylation yields 2',5'-A-A-3'-amino (compound 43, Table 5).

EXAMPLE 4

Preparation of 5'-O-p-methoxytrityladenylyl (2',5')adenylyl(2',5')adenosine 0.01 Mmole of N⁶-benzoyl-3'-O-t-butyldimethyl silyl-5'-O-p-methoxytrityladenylyl(2'-o-chlorophenyl-5')N⁶-benzoyl-3'-O-t-butyldimethylsilyladenylyl(2'-o-chlorophenyl-5')N⁶,N⁶-2'-0,3'-O-tetrabenzoyladenosine prepared according to the method of Charubala, R., Uhlmann, E., and Pfleiderer, W., Liebigs Ann. Chem., 2392 (1981) was treated according to the deprotection procedure of Example 1 except that the last step of acetic acid treatment was omitted. The product, 2',5'-trityl-A₃ (compound 44, Table 5) was isolated, purified by DEAE-Sephadex A-25 chromatography, and lyophilized to form the amorphous pure compound 44 as a powder in 85% yield.

EXAMPLE 5

Preparation of 5'-O-p-methoxytrityl-3'-deoxyadenylyl (2',5')3'-deoxyadenylyl(2',5')3'-deoxyadenosine 0.01 Mmole of N⁶-benzoyl-5'-O-p-methoxytrityl-3'--deoxyadenylyl(2'-o-chlorophenyl-5')N⁶-benzoyl-3'-deoxyadenylyl(2'-o-chlorophenyl-5')N⁶,N⁶,2'-O-tribenzoyl-3'-deoxyadenosine prepared according to the method of Charubala, R., and Pfleiderer, W., Tetrahedron Lett. 21, 4077 (1980) was treated according to the deprotection procedure of Example 1 except that the steps of treatment with tetrabutylammonium fluoride and acetic acid were omitted. The product, 2',5'-trityl-C₃ (compound 45, Table 5) was isolated, purified by DEAE-Sephadex A-25 chromatography and lyophilized to form the amorphous pure compound.

The 5'-monophosphates of the trimer core molecules of the present invention may be prepared from the fully blocked 2',5'-trinucleosidediphosphoditriester by detritylation as in Example 1 followed by reaction with di-p-nitrophenylethylphosphoryl chloride. Extraction, chromatography and deblocking according to Example 1 results in isolation of the 5'-monophosphate trimers. The preparation is exemplified in the method of Example 6.

EXAMPLE 6

Preparation of 5'-O-phosphoryl-3'-deoxyadenylyl (2',5')3'-deoxyadenylyl(2',5')3'-deoxyadenosine 0.1 Mmole of N⁶-benzoyl-5'-O-p-methoxytrityl-3'--deoxyadenylyl(2'-o-chlorophenyl-5')N⁶-benzoyl-3'-deoxyadenylyl(2'-o-chlorophenyl-5')N⁶,N⁶,2'-O-tribenzoyl-3'-deoxyadenosine is prepared from 3'-deoxyadenosine by benzoylation, 5'-tosylation, and 2'-phorsphorylation, with formation of the dinucleoside phosphotriester, N⁴-benzoyl(2-o-chlorophenylphosphoryl-5)3'-deoxyadenosine, by treatment of the reaction products N⁶-benzoyl(2-triethylammonium-o-chlorophenylphosphoryl-5)-5'-tosyl-3'-deoxyadenosine and 2'-cyanoethylphosphoryl-o-chlorophenyl-3'-deoxyadenosine with triisopropylbenzenesulfonyl-nitro-1,2,4-triazolide. The fully blocked dimer thus formed is condensed with N⁶,2'-O-dibenzoyl-3'-deoxyadenosine to form the trimer. 0.1 mM of this trimer prepared according to the method of Charubala, R., and Pfleiderer, W., Tetrahedron Lett. 21, 4077 (1980) was treated with 2 ml of a solution of 2% p-toluenesulfonic acid in dichloromethane/methanol (7/3, v/v) for 30 minutes at room temperature to remove the p-methoxytrityl group. Purification by silica gel chromatography on a preparative plate with chloroform/methanol (95/5, v/v) gave a 90% yield of the 5'-deprotected analog.

This product was dissolved in 1 l of absolute pyridine and treated with 0.27 mmole of di-p-nitrophenylethylphosphoryl chloride as described by Himmelsbach, F., and Pfleiderer, W., Tetrahedron Lett. 23, 4793 (1982) for 1 hr at room temperature. After dilution with 15 ml of chloroform, the reaction mixture was extracted three times with phosphate buffer pH 7. The organic layer was dried over sodium sulfate, filtered, evaporated and coevaporated three times with 10 ml of toluene each time. The residue was purified by silica gel chromatography on preparative plates in chloroform/methanol (9/1, v/v) to yield 81% of 5'-O-di-p-nitrophenylet hylphosphoryl-N⁶-benzoyl-3'-deoxyadenylyl(2'-o-chlorophenyl-5')N⁶-benzoyl-3'-deoxyadenylyl(2'-o-chlorophenyl-5')N⁶,N⁶,2'-O-tribenzoyl-3'-deoxyadenosine in the form of an amorphous solid.

0.01 Mmole of the latter material was treated with p-nitrobenzaldoxime according to the deprotection procedure of Example 1 to remove o-chlorophenyl blocking groups. After evaporation to dryness and several coevaporations with absolute pyridine, the deprotected product was dissolved in 10 ml of a 0.5M solution of diazabicyclo[4.3.0]undecene in absolute pyridine and stirred for 36 hours at room temperature to cleave the p-nitrophenylethyl group by β-elimination. The solution was again evaporated and then treated with 20 ml of concentrated ammonium hydroxide for 24 hours at room temperature. Purification and isolation of the trimer core 5′-monophosphate (compound 46, Table 5) was achieved by DEAE-Sephadex chromatography and lyophilization of the main fraction.

The tetramer core molecules of the present invention may be prepared by following the method of Examples 7 or 8.

EXAMPLE 7

Preparation of adenylyl(2′,5′)adenylyl(2′,5′)3′-deoxyadenylyl(2′,5′)3′-deoxyadenosine 0.5 Mmole of fully-protected compound 47 having the formula (VI) and 0.4 mmole of $N^6$-benzoyl-3′-deoxyadenylyl (2′-o-chlorophenyl-b 5′)$N^6$,2′-O-dibenzoyl-3′-deoxyadenosine (compound 24, Table 3) were dissolved in 5 ml of absolute pyridine.

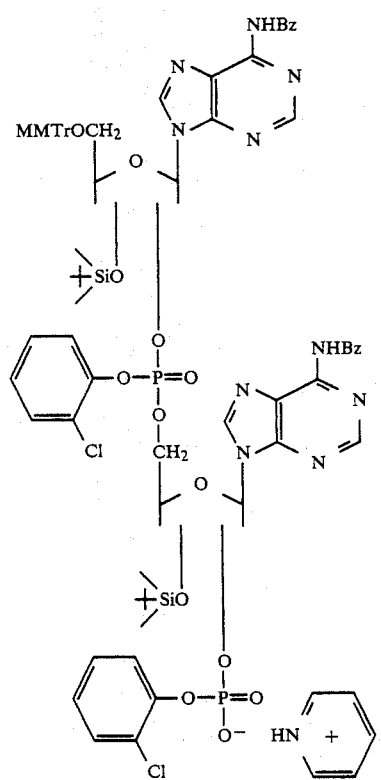

Reactant (VI)

Following addition of 1 mmole of 2,4,6-triisopropylbenzenesulfonyl chloride and 3 mmole of 1-methylimidazone, the mixture was stirred for 2 hrs at room temperature. The solution was diluted with 400 ml of chloroform, washed twice with 400 ml of water, then the organic layer was dried over sodium sulfate, filtered and evaporated to dryness. The residue was coevaporated twice with 50 ml of toluene. Purification was achieved by chromatography on a silica gel column (20×2.5 cm) first with chloroform and then with a gradient of chloroform/methanol of 99/1 to 98/2 (v/v). On evaporation, the main fraction gave compound 48 (Table 6) as a solid form in 80% yield. Compound 48 is a fully blocked 2′,5′-tetranucleosidetriphosphotritriester according to the general formula of tetramer core (VII), below. Deprotection of the blocking groups was performed by the procedure of Example 1 to yield 2′,5′-A—A—C—C (compound 49, Table 6). DEAE-Sephadex chromatography, evaporation and lyophilization resulted in an amorphous solid in 80% yield.

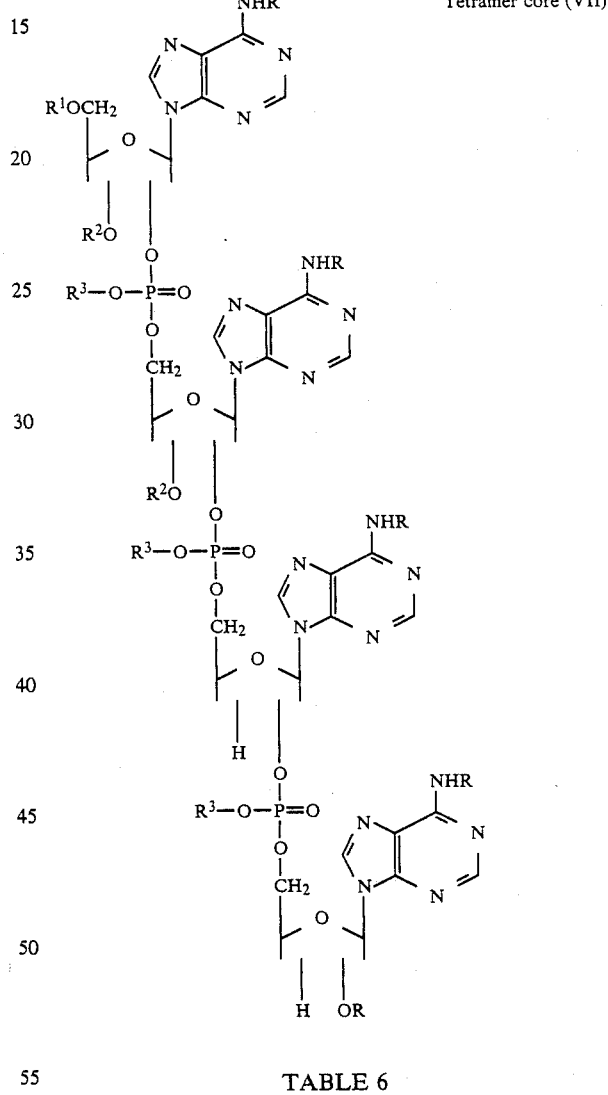

Tetramer core (VII)

TABLE 6

| Compound No. | R | $R^1$ | $R^2$ | $R^3$ |
|---|---|---|---|---|
| 48 | Bz | MMTr | Si—⫮— | ⌬Cl |
| 49 | H | H | H | H |

EXAMPLE 8

Preparation of 3'-deoxyadenylyl(2',5')3'-deoxyadenylyl(2',5')3'-deoxyadenylyl(2',5')3'-deoxyadenosine 0.1 Mmole of N⁶-benzoyl-5'-O-p-methoxytrityl-3'-deoxyadenylyl(2'-o-chlorophenyl-5')N⁶-benzoyl-3'-deoxyadenylyl(2'-o-chlorophenyl-5')N⁶,N⁶,2'-O-tribenzoyl-3-deoxyadenosine (compound 50, Table 7), a fully-blocked 2',5'-trinucleosidediphosphoditriester according to the general formula of reactant (VIII),

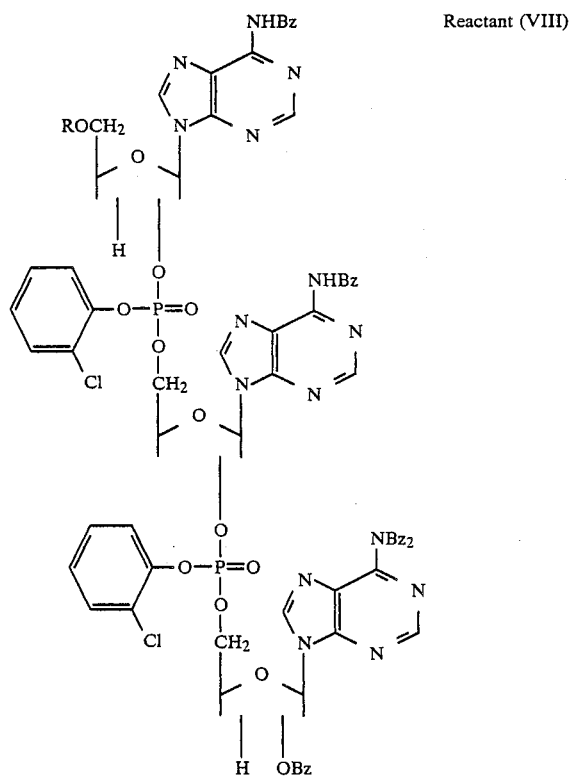

Reactant (VIII)

TABLE 7

| Compound No. | R |
|---|---|
| 50 | MMTr |
| 51 | H | was treated with 2 ml of a 2% solution fo p-toluenesulfonic acid in dichloromethane/methanol (4/1, v/v) for 30 minutes at room temperature. The reaction was stopped by adding 20 ml of phosphite buffer pH 7. The solution was extracted several times with 200 ml of chloroform. The organic layer was washed with water, dried over sodium sulfate, filtered and evaporated to a small volume for purification on preparative silica gel plates in chloroform/methanol (95/5, v/v). The main band was eluted by chloroform/methanol (4/1, v/v) to give the 5'-detritylated compound 51 (Table 7) upon evaporation in 80% yield.

0.05 Mmole of compound 51 (Table 7) was then condensed with 0.1 mmole of pyridinium N⁶-benzoyl-5'-O-p-methoxytrityl-3'-deoxyadenosine-2'-(2-o-chlorophenyl)phosphate (compound 2, Table 1) in 0.6 ml of absolute pyridine in the presence of 0.2 mmole of 2,4,6-triisopropylbenzenesulfonyl chloride and 0.6 mmole of 1-methylimidazole for 2 hrs at room temperature. The solution was diluted with 100 ml of chloroform, washed twice with water, dried over sodium sulfate and evaporated to a small volume for separation on preparative silica gel plates in chloroform/methanol (95/5, v/v). The main band was eluted with chloroform to give the fully-protected 2',5'-tetranucleosidetriphosphotritriester compound 52 (Table 8, below) as an amorphous solid upon evaporation in 84% yield.

The blocking groups of compound 52 were removed according to the procedure of Example 1, followed by DEAE-Sephadex chromatography and lyophilization. Tetramer core 2',5'-C—C—C—C (compound 53, Table 8) resulted as an amorphous solid in 70% yield. The structure of compound 53 is according to the general formul of tetramer core (IX).

The 5'-O-monophosphates of the tetramer core molecules of the present invention may be prepared from the fully blocked 2',5'-tetranucleosidetriphosphotritriester by 5'-detritylation as in Example 1 followed by reaction with di-p-nitrophenylethylphosphoryl chloride. Extraction, chromatography and deblocking according to Example 1 results in isolation of the 5'-O-monophosphate tetramers. The preparation is exemplified in Example 6.

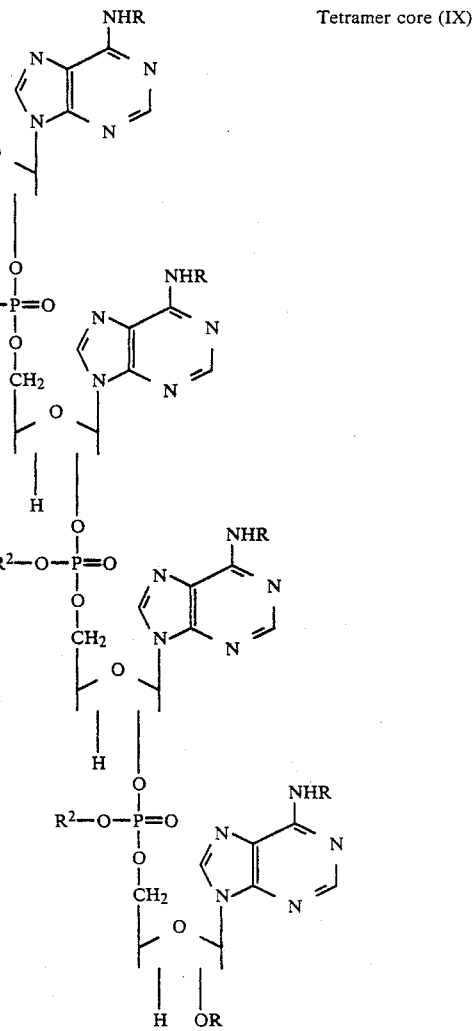

Tetramer core (IX)

TABLE 8

| Compound No. | R | R¹ | R² |
|---|---|---|---|
| 52 | Bz | MMTr | 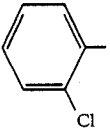 |
| 53 | H | H | H |

The 5'-diphosphate and 5'-triphosphate of the trimer and tetramer core molecules of the present invention may be prepared by adding 0.5 mM of tributylammonium pyrophosphate dissolved in 5 ml of dimethylformamide to 0.1 mM of monophosphorylated core as the anhydrous tributylammonium salt in 1 ml of dimethylformamide and 0.5 mM of 1,1'-carbonyldiimidazole. After 20 hours at room temperature, the reactants are treated with 5 ml of methanol, evaporated to dryness and chromatographed on a 2×20 cm DEAE cellulose column. The 5'-di and triphosphates are isolated following a linear gradient (0–0.4M in 3 l at pH 7.5) of triethylammoniumbicarbonate. This is the method of Hoard, D. E., and Ott, D. G., J. Amer. Chem. Soc. 87, 1785–1788 (1965), which is incorporated herein by reference. The 5'-diphosphates and 5'-triphosphates may then be purified by DEAE-Sephadex A25 and Sephadex The 2',5'-oligoadenylate analogs, 2',5'-C—C—C—C, 2',5'-I$_3$, 2',5'-A—A-ara-A, 2',5'-A—A—Tu, and 2',5'-Xylo-A$_3$, were all potent inhibitors of TMV replication in *N. glutinosa* leaves. 2',5'-C—C—C—C, 2',5'-A—A-ara-A, and 2',5'-A—A—Tu were more potent inhibitors than the naturally occurring 2',5'-adenylate trimer core. The trimer and tetramer core Xylo-A$_3$ and Xylo-A$_4$ are synthesized by treating N$^6$-3'-O-dibenzoylated xylofuranose with t-butyldimethylsilylchloride to yield the silylated derivative of N$^6$-3'-O-dibenzoylated xylofuranose which is debenzoylated with sodium methoxide to form the 2'-silyl derivative. The primary hydroxyl of the 2'-silyl derivative is protected with a monomethoxytrityl group and the resulting 5'-tritylated-2'-silyl derivative is reacted with an equimolar equivalent of benzoic anhydride dissolved in pyridine in the presence of 4-dimethylaminopyridine to yield the N$^6$ and 3-O-benzoylated-5'-tritylated-2'-silylated derivative. Removal of the t-butyldimethylsilyl group with tetrabutylammonium fluoride gives the N$^6$ and 3-O-dibenzoylated-5'-tritylated derivative which is successively benzoylated and detritylated to produce N$^6$,2',3'-O-tribenzoylxyloadenosine.

The previous N$^6$ and 3-O-dibenzoylated-5'-tritylated derivative is also reacted with an excess of o-chlorophenylphosphoro-di-(1,2,4-triazolide) in an acetonitrile-pyridine mixture followed by a reaction with aqueous triethylamine to form the 2'-phosphotriester. The phosphotriester is condensed with N$^6$,2',3'-O-tribenzoylxyloadenosine in the presence of 1-mesitylenesulfonyl-3-nitro-1,2,4-triazole to yield the fully protected dinucleosidephosphotriester which is detritylated by treatment with p-toluenesulfonic acid in a mixture of chloroform and methanol (4:3). A final condensation between the detritylated product and the phosphotriester and purification by silica gel chromatography yields the fully protected trinucleosidediphosphotriester (blocked trimer core). The fully deblocked trimer core is obtained by treatment of the blocked trimer core with tetramethylguanidinium-syn-4-nitrobenzaldoximate, aqueous ammonia, and 80% acetic acid. Preparation of the trimer core 2',5'-Xylo-A$_3$ and tetramer core 2',5'-xylo-A$_4$ is reported in Grosselin, G. and Imbach, J.-L., Tetrahedron Lett. 22, 4699 (1981), which is incorporated herein by reference.

When the 3'-hydroxyl function of the adenylate residues of 2',5'-adenylate trimer core was replaced with a 3'-hydrogen atom, the modified analog, 2',5'-C—C—C, was the most potent inhibitor of TMV replication. This molecule completely inhibited TMV replication for 96 hours, compared to the naturally occurring 2',5'-adenylate trimer core which inhibited TMV replication for only 48 hours. 2',5'-C—C—C also inhibited HSV-1 replication, EBV-induced morphological transformation of lymphocytes and ascites tumor growth. It inhibited solid tumor growth.

2',5' trimer cores containing adenylate and cordycepin residues with the general formulae, 2',5'-A—A—C, 2',5'-A—C—C, 2',5'-C—C—A, and 2',5'-C—A—C, were synthesized as described in the above examples. 2',5'-A—A—C was as good as 2',5'-C—C—C in inhibiting ascites tumor growth in animals. However, 2',5'-A—C—C was without effect. Thus, a change in a single adenylate residue may significantly impact on the spectrum of biological activity.

When the 2',5'-adenylate trimer core was modified at the 2'-terminus, i.e., 2',5'-A—A—Tu or 2',5'-A—A-ara-A, there was excellent inhibition of TMV replication. These 2'-terminally modified molecules are also extremely effective in preventing EBV-induced morphological transformation. The analogs 2',5'-A—A-3'-amino, 2',5'-A—A—A-3'-O-pentyl and 2',5'-A—A—A-3'-O-heptyl are believed to inhibit vaccinia virus infected cells.

The 5'-terminus of the 2',5'-adenylate and 2',5'-cordycepin cores was modified by the replacement of the 5'-hydrogen on the hydroxyl with a p-methoxytrityl group. The 2',5'-trityl-A$_3$ analog is as potent an inhibitor of EBV-induced morphological transformation as the cordycepin core (See Table 13).

When the 2',5'-A$_3$ molecule was modified at the 2',5'-adenylyl residues to form 2',5'-A$_{(Si)}$-A$_{(Si)}$-A, there was a marked inhibition of EBV-induced transformation of infected lymphocytes.

Structural modifications of the 2',5'-oligoadenylate molecule at the 2'-terminal nucleoside, aglycon and/or ribosyl moiety have provided molecules that are potent inhibitors of tumor growth in mammals and virus replication in plants and mammals. These synthetic molecules are biologically more active and metabolically more stable than the naturally occurring 2',5'-oligoadenylate molecule. Moreover, they show no cytotoxicity.

The antiviral activity of the compounds of the present invention is demonstrated by the following experiments in which any of the most preferred compounds of the invention and their 5'-mono-, di-, and triphosphate counterparts may be substituted for any of the analogs in the following experiments with the efficacy disclosed for such compounds in the specification.

EXAMPLE 9

Plant Material Treatment and Measurement of Infectivity

The effectiveness of 2',5'-oligoadenylate analogs of the present invention against plant virus is demonstrated using TMV-infected leaves of *N. glutinosa* and *N. tabacum*.

The growth of *N. glutinosa*, *N. tabacum* Var. "Samsun, *N. tabacum* cv. Samsun NN, and preparation and inoculation of protoplasts was carried out according to the method as described by Loebenstein, G., and Gera, A., Virology 114, 132-139 (1981) and Loebenstein, G., Gera. A., Barnett, A., Shabtai, S., and Cohen, J., Virology 100, 110-115 (1980). To evaluate the effect of 2′,5′ oligomers on TMV replication, various concentrations of oligomer were added to 10 ml of protoplast suspension ($1 \times 10^5$ cells/ml) at various times after inoculation with TMV. Protoplasts were incubated at 25° C. under continuous illumination of about 1500 Lx. At various times protoplasts were collected by centrifugation and homogenized. The homogenate was inoculated onto half-leaves of *N. glutinosa* plants and compared to a standard solution of purified TMV on the opposite half-leaves. Lesion counts were adjusted to $10^6$ live protoplasts and calibrated. Control protoplasts (no nucleotides added) were assayed simultaneously. Assays for antiviral activity on TMV-infected tobacco leaf discs were performed by enzyme-linked immunosorbent assay (ELISA).

The ability of the 2′,5′-adenylate analog cores, nucleosides, and nucleotides to inhibit TMV replication in the intact plant was determined by infectivity tests as follows. Solutions containing 5 μg/ml TMV, 0.1 g carborundum (200 mesh), and 2′,5′-adenylate analog cores, nucleosides, or nucleotides were applied onto half-leaves of *N. glutinosa* (Loebenstein, G., and Gera, A., Virology 114, 132-139 (1981). The remaining half-leaves were controls (inoculated with a solution containing no active compound). The infection was allowed to proceed 48 hr under continuous illumination of about 1500 Lx at which time local virus lesions appeared. Inhibition of TMV replication was calculated as the percent of local lesions produced in 2′,5′-oligoadenylate analog-treated half-leaves compared to control half-leaves.

Inhibition Of TMV Replication By 2′,5′-Adenylate Analog Cores In Tobacco Protoplasts And Leaf Discs The effect of 2′,5′-oligomer cores on the inhibition of TMV replication in protoplasts was measured. At $1 \times 10^{-8}$M, 2′,5′-adenylate trimer core in protoplast medium inhibited TMV replication 53% after 72 hr (Table 9). The inhibition of virus replication by the 2′,5′-adenylate trimer core was dose dependent. 2′,5′-adenylate trimer core and 2′,5′-cordycepin trimer core inhibited TMV replication 93% and 96%, respectively, at $1 \times 10^{-7}$M. 3′,5′-Adenylate trimer core was of similar potency to AMP. The 2′,5′-inosine trimer core caused about 50% inhibition of TMV replication at $1 \times 10^{-7}$M. Adenosine, AMP, cordycepin, 3′dAMP, and inosine (possible degradation products) were less inhibitory. A maximum antiviral effect was obtained when the 2′,5′-adenylate analog cores were added earlier than 5 hr after inoculation with TMV (Table 10). The antiviral effect was decreased when 2′,5′-adenylate analog cores were added 5 and 12 hr after infection.

TABLE 9

The Inhibition of TMV Replication in Tobacco Protoplasts by 2′,5′-Adenylate Trimer Core and Analogs[a]

| Nucleotide Added | Concentration (M) | Inhibition[b] After 24 hr (%) | After 48 hr (%) | After 72 hr (%) |
|---|---|---|---|---|
| No addition | — | 0 | 0 | 0 |
| 2′,5′-A₃ | $1 \times 10^{-8}$ | 48 (P < 0.01) | 41 (P < 0.01) | 53.0 (P < 0.01) |
|  | $1 \times 10^{-7}$ | 92 (P < 0.01) | 93 (P < 0.01) | 92 (P < 0.01) |
| 3′,5′-A₃ | $1 \times 10^{-7}$ | 27 (P < 0.01) | 38 (P < 0.01) | ND |
| Adenosine | $1 \times 10^{-7}$ | 14 (P < 0.01) | 0 | ND |
| AMP | $1 \times 10^{-7}$ | 22 (P < 0.01) | 33 (P < 0.01) | ND |
| 2′,5′-C—C—C | $1 \times 10^{-7}$ | 95 (P < 0.01) | 96 (P < 0.01) | ND |
| Cordycepin | $1 \times 10^{-7}$ | ND[c] | 21 (P < 0.01) | 32 (P < 0.01) |
| 3′dAMP | $1 \times 10^{-7}$ | ND | 41 (P < 0.01) | 45 (P < 0.01) |
| 2′,5′-I₃ | $1 \times 10^{-7}$ | 53 (P < 0.01) | 54 (P < 0.01) | ND |
| Inosine | $1 \times 10^{-7}$ | ND | 22 (P < 0.01) | 25 (P < 0.01) |

[a]2′,5′- or 3′,5′-adenylate trimer cores, nucleosides and nucleotides were added to the TMV-infected protoplasts within 3 hr of infection.
[b]Average of four experiments. Inhibition of TMV replication observed by the 2′,5′-adenylate cores, nucleosides and nucleotides was calculated as the percent of local lesions produced in *N. glutinosa* treated by homogenates of protoplasts compared to non-treated protoplasts.
[c]Not determined.

TABLE 10

Inhibition Of TMV Replication In Tobacco Protoplasts Treated With 2′,5′-Adenylate Trimer Core And Analog At Various Times After Infection

| Compound Added[a] | Time of addition (hr after inoculation) Inhibition[b] | | |
|---|---|---|---|
|  | after 0 hr (%) | after 5 hr (%) | after 12 hr (%) |
| No addition | 0 | 0 | 0 |
| 2′,5′-A₃ | 78 (P < 0.01) | 59 (P < 0.01) | 44 (P < 0.01) |
| 3′,5′-A₃ | 31 (P < 0.01) | 24 (P < 0.01) | 23 (P < 0.01) |
| 2′,5′-C—C—C | 78 (P < 0.01) | 66 (P < 0.01) | 53 (P < 0.01) |
| 2′,5′-I₃ | 60 (P < 0.01) | 50 (P < 0.01) | 37 (P < 0.01) |

[a]Final concentration of 2′,5′-oligoadenylate trimer cores in protoplast medium was $5 \times 10^{-8}$ M.
[b]Inhibition of TMV replication was determined 48 hr after infection and calculated as in Table 9 footnote b.

EXAMPLE 10

Inhibition Of TMV Replication By 2′,5′-Adenylate Analog Cores With Increasing Time The kinetics of the inhibition of TMV-replication by the 2′,5′-A₃ core and 2′,5′-C—C—C in infected leaf discs was determined as follows.

Leaves were mechanically inoculated with purified virus (5 μg/ml in 0.1M sodium phosphate buffer, pH 7.6, containing 0.1 g/ml of carborundum). Leaf discs (6.5 mm diameter) were punched out of the inoculated leaves and placed in a beaker containing 0.01M sodium phosphate, pH 7.6. Groups of 20 discs were selected at random from this common pool and placed into separate petri dishes, each containing 20 ml of sodium phosphate buffer. Buffer was aspirated from the dishes after 1 hour. The TMV-inoculated tobacco leaf discs were treated for one hr with 200 nM 2',5'-A$_3$ or 200 nM 2',5'-C—C—C. The discs were washed and the infection was allowed to proceed at room temperature under constant illumination. The discs were then homogenized and the TMV content was determined by ELISA. Virus protection was inhibited for 48 hr by 2',5'-A$_3$ core, but the inhibitory effect gradually diminished after 48 hr. However, TMV inhibition by 2',5'-C—C—C was noted for 96 hr (See Figure). The extended inhibitory activity of the 2',5'-C—C—C compared to the naturally occurring adenylate core may be due to increased stability of the analog, an effect of increased uptake, or a different inhibitory mechanism.

Effect Of 2',5'-A$_3$ And Its Analogs on TMV Replication In Intact Plants

2',5'-A$_3$, 2',5'-C—C—C, 2',5'-xylo-A$_3$, 2',5'-I$_3$, 2',5'-A—A-ara-A, and 2',5'-A—A—Tu were potent inhibitors of TMV replication when applied to leaves of *N. glutinosa* at $1 \times 10^{-6}$M in the TMV-infecting solution. The aforementioned trimer cores inhibited the formation of local lesions following TMV infection by 89–99% (Table 11). The nucleosides and nucleotides were not antivirally active, or they exhibited negligible activity at $1 \times 10^{-6}$M. 2',5'-A$_3$, 2',5'-C—C—C, and 2',5'-I$_3$ inhibited TMV replication in a dose-dependent manner. 2',5'-I$_3$ was not as good (68% inhibition at $1 \times 10^{-6}$M) as 2',5'-A$_3$ and 2',5'-C—C—C (91% and 93% inhibition at $1 \times 10^{-6}$M, respectively) (Table 12). Non-infected plants were treated with $1 \times 10^{-6}$M of 2',5'-A$_3$, 2',5'-C—C—C, 2',5'-A—A-ara-A, and 2',5'-A—A—Tu. No toxicity (chlorosis or necrosis) was observed during the two week period tested.

TABLE 11

Effect of 2',5'-A$_3$, 2',5'-Adenylate Core Analogs, Nucleosides and Nucleotides on TMV Replication in *N. glutinosa* Leaves

| Addition[a] | Inhibition[b] % |
|---|---|
| No Addition | 0 |
| 2',5'-A$_3$ | 93 (P < 0.01) |
| 2',5'-C—C—C | 99 (P < 0.01) |
| 2',5'-I$_3$ | 92 (P < 0.01) |
| 2',5'-A—A—ara-A | 94 (P < 0.01) |
| 2',5'-A—A—Tu | 95 (P < 0.01) |
| 2',5'-Xylo—A$_3$ | 89 (P < 0.01) |
| AMP | 10 |
| Cordycepin monophosphate | 0 |
| IMP | 10 (P < 0.01) |
| Ara-AMP | 0 |
| TuMP | 0 |
| Adenosine | 0 |
| Cordycepin | 0 |
| Inosine | 0 |
| Ara-A | 0 |
| Tubercidin | 0 |
| Xylo A | 0 |

[a]All additions were at $1 \times 10^{-6}$ M in the infecting solution.
[b]Inhibition of TMV replication was determined 48 hr after infection and calculated as in Table 9, footnote b.

TABLE 12

Effect of Various Concentrations of 2'5'-A$_3$, 2',5'-C—C—C, and 2', 5'-I$_3$ On Replication in *N. glutinosa* Leaves

| Oligonucleotide Added | Concentration (M) | Inhibition (%) |
|---|---|---|
| No addition | — | 0 |
| 2',5'-A$_3$ | $1 \times 10^{-6}$ | 91 (P < 0.01) |
| | $1 \times 10^{-7}$ | 80 (P < 0.01) |
| | $1 \times 10^{-8}$ | 75 (P < 0.01) |
| 2',5'-C—C—C | $1 \times 10^{-6}$ | 93 (P < 0.01) |
| | $1 \times 10^{-7}$ | 84 (P < 0.01) |
| | $1 \times 10^{-8}$ | 76 (P < 0.01) |
| 2',5'-I$_3$ | $1 \times 10^{-6}$ | 68 (P < 0.01) |
| | $1 \times 10^{-7}$ | 50 (P < 0.01) |
| | $1 \times 10^{-8}$ | 36 (P < 0.01) |

EXAMPLE 11

Inhibition of EVB-Induced Morphological Transformation of Peripheral Blood Leukocytes The morphological transforming efficiencies of EBV-exposed lymphocytes were determined by colony formation in a transformed centers assay (Doetsch, et al, Proc. Natl. Acad. Sci. USA 78, 6699 (1981)). Cells were serially diluted into individual wells of a microtiter plate. Colonies that developed within 4 weeks were counted with an inverted tissue culture microscope, and the initial colony-forming unit per seeded cell was calculated. Transformed colonies were measured 4–6 weeks after infection with EVB and simultaneous treatment with human leukocyte interferon (IFN-α) or 2',5'-adenylate analog core trimers. 2',5'-Trityl-A$_3$, 2',5'-A—A-ara-A, 2',5'-A—A—Tu, 2',5'-Xylo-A$_3$, 2',5'-Xylo-A$_4$, 2',5'-C—C—C, 2',5'-A$_{(Sf)}$-A$_{(Sf)}$-A and 2',5'-A$_3$ core inhibited the appearance of transformed colonies. Transformation was inhibited in a dose-dependent manner with respect to cell number and interferon or 2',5'-adenylate analog core concentration. The data are shown in Table 13, demonstrating that marked changes in biological activity may result from subtle structural modifications.

TABLE 13

Effects of 2',5'-Adenylate Analog Cores On EBV-Induced Transformation Of Adult Peripheral Blood Leukocytes[a]

| 2',5'-Adenylate analog (300 μM) | Transformed centers assay[b] | | | |
|---|---|---|---|---|
| | 250 | 25 | 2.5 | 0.25 |
| Experiment 1 | | | | |
| None | 2/2 | 2/2 | 2/2 | 1/2 |
| 2',5'-A—C—C | 2/2 | 2/2 | 2/2 | 2/2 |
| 2',5'-A—A—C | 2/2 | 2/2 | 2/2 | 2/2 |
| 2',5'-trityl—A$_3$ | 1/2 | 0/2 | 0/2 | 0/2 |
| 2',5'-trityl—C$_3$ | 2/2 | 2/2 | 2/2 | 2/2 |
| 2',5'-A—A—ara-A | 0/2 | 0/2 | 0/2 | 0/2 |
| 2',5'-A—A—Tu | 0/2 | 0/2 | 0/2 | 0/2 |
| IFN-α (100 units/ml) | 0/2 | 0/2 | 0/2 | 0/2 |
| Experiment 2 | | | | |
| None | 2/2 | 2/2 | 2/2 | 0/2 |
| 2',5'-Xylo—A$_3$ | 2/2 | 0/2 | 0/2 | 0/2 |
| 2',5'Xylo—A$_4$ | 1/2 | 1/2 | 0/2 | 0/2 |
| 2',5'-A—A—Tu | 0/2 | 0/2 | 0/2 | 0/2 |
| 2',5'-C—C—C | 1/2 | 0/2 | 0/2 | 0/2 |
| 2',5'-A$_{(Sf)}$—A$_{(Sf)}$—A | 0/2 | 0/2 | 0/2 | 0/2 |
| IFN-α (100 units/ml) | 0/2 | 0/2 | 0/2 | 0/2 |
| 2',5'-A$_3$ | 2/2 | 1/2 | 0/2 | 0/2 |

[a]Pulsed with compound for 24 hrs, then serially diluted to indicated cell concentrations.
[b]Cell transformants per replicate exposure at cells $\times 10^3$ per well; determined by colony formation in replicate wells of microtiter plates 4–6 wk after EBV exposure.

EXAMPLE 12

Inhibition Of Ascites Tumor Growth In Animals By Derivatives Of 2',5'-Oligoadenylate Core Female Swiss ICR mice (25 g, 6-8 weeks old) were injected intraperitoneally with $1.5-2\times10^7$ Ehrlich ascites tumor cells per mouse. Animal weight gains were monitored at 2 day intervals. Treatments with nucleosides or 2',5'-adenylate core analogs were accomplished by intraperitoneal injection in 0.5 ml phosphate buffered saline 4 days after ascites cell implantation. Inhibition of tumor growth is expressed in Table 14 as percent of initial weight.

TABLE 14

Inhibition of Ascites Tumor Growth by 2',5'-Adenylate Core Analogs

| Treatment | Dose µmol/100 g body weight | Percent Initial Body Weight After 11 Days % |
|---|---|---|
| Control[a] | — | 100 |
| None[b] | — | 139 |
| 2',5'-C—C—C | 1 | 126 |
|  | 2 | 112 |
|  | 5 | 98 |
|  | 10 | 95 |
| 2',5'-A$_3$ | 5 | 144 |
|  | 10 | 139 |
| 2',5'-C—C—C—C | 2 | 101 |
|  | 5 | 98 |
| 2',5'-A—A—C | 5 | 109 |
|  | 10 | 108 |
| 2',5'-A—C—C | 5 | 144 |
|  | 10 | 138 |
| 3',5'-A$_3$ | 2 | 124 |
|  | 5 | 111 |
| 2',5'-I$_3$ | 10 | 100 |

[a]non-tumor bearing animal
[b]tumor bearing animal, no 2',5'-adenylate core analog treatment At 10 µmole 2',5'-adenylate core analog per 100 g body weight, 2',5'-A—A—C, 2',5'-C—C—C, 2',5'-C—C—C—C and 2',5'-I$_3$ completely inhibited ascites tumor growth in mice for 11 days. After 60 days, there was continued inhibition of tumor growth, with no tumor detectable. In view of the inhibitory activity of 2',5'-C—C—C, 2',5'-A—A—C and 2',5'-C—C—C—C, it was expected that 2',5'-A—A—C would also be inhibitory. However, there was no inhibition of tumor growth by 2',5'-A—C—C (see Table 14).

All references herein cited with respect to synthetic or analytical procedures are incorporated herein by reference.

The present invention may be embodied in other specific forms without departing from the spirit or essential attributes thereof and, accordingly, reference should be made to the appended claims, rather than to the foregoing specification, as indicating the scope of the invention.

We claim:

1. A compound selected from the group consisting of adenlylyl(2',5')3'-deoxyadenylyl(2',5')3'-deoxyadenosine and the 5' mono, di-, and triphosphate thereof.

2. A compound selected from the group consisting of 3'-deoxyadenylyl(2',5')adenylyl(2',5')3'-deoxyadenosine and the 5' mono-, di-, and triphosphate thereof.

3. A compound selected from the group consisting of the 5' mono-, di-, and triphosphate of 3'-deoxyadenylyl(2',5')3'-deoxyadenylyl(2',5')(R)-3-(2-deoxy-β-D-erythropentofuranosyl)-3,6,7,8-tetrahydroimidazo[4,5-d][1,3]diazepine-8-ol and 5' mono-, di-, and triphosphates thereof.

4. A compound selected from the group consisting of adenyl(2',5')adenyl(2',5')3'-amino-3'-deoxyadenosine and the 5' mono-, di-, and triphosphate thereof.

5. A compound selected from the group consisting of adenylyl(2',5')adenylyl(2',5')3'-O-pentyladenosine, adenylyl(2',5')adenylyl(2',5')3'-O-hexyladenosine, adenylyl(2',5')adenylyl(2',5')3'-O-heptyladenosine and the 5' mono-, di-, and triphosphates thereof.

6. A compound selected from the group consisting of adenylyl(2',5')adenylyl(2',5')3'-deoxyadenylyl(2',5')3'-deoxyadenosine and the 5' mono-, di-, and triphosphate thereof.

7. A compound selected from the group consisting of 3'-O-t-butyldimethylsilyladenylyl(2',5')3'-O-t-butyldimethylsilyladenylyl(2',5')adenosine and the 5' mono-, di-, and triphoshate thereof.

8. 3'-O-t-butyldimethylsilyladenylyl(2',5')3'-O-t-butyldimethylsilyladenylyl(2',5')adenosine, a compound of claim 7.

9. A compound selected from the group consisting of adenyl(2',5')adenylyl(2',5')tubercidin and the 5' mono-, di-, and triphosphate thereof.

10. Adenylyl(2',5')adenylyl(2',5')tubercidin, a compound of claim 9.

11. A compound selected from the group consisting of 5'-O-p-methoxytrityl-3'-deoxyadenylyl(2',5')3'-deoxyadenylyl(2',5')3'-deoxyadenosine and the 5' mono-, di-, and triphosphate thereof.

12. A compound selected from the group consisting of 5'-O-p-methoxytrityladenylyl(2',5')adenylyl(2',5')adenosine and the 5' mono-, di-, and triphosphate thereof.

13. 5'-O-p-methoxytrityl-3'-deoxyadenylyl(2',5')3'-deoxyadenylyl(2',5')3'-deoxyadenosine, a compound of claim 11.

14. 5'O-p-methoxytrityladenylyl(2',5')adenylyl(2',5')adenosine, a compound of claim 12.

15. A compound selected from the group consisting of xyloadenylyl(2',5')xyloadenylyl(2',5')xyloadenylyl(2',5')xyloadenosine and the 5' mono-, di-, and triphosphate thereof.

16. A compound according to claim 15 wherein the compound is xyloadenylyl(2',5')xyloadenylyl(2',5')xyloadenylyl(2',5')xyloadenosine.

* * * * *